(12) United States Patent
Gray Wood

(10) Patent No.: US 6,789,799 B2
(45) Date of Patent: Sep. 14, 2004

(54) KISSING SHIELD GAME AND METHOD OF USE THEREOF

(76) Inventor: Deloris Gray Wood, R.R. 5, Box 134, Salem, MO (US) 65560

( * ) Notice: Subject to any disclaimer, the term of this patent is extended or adjusted under 35 U.S.C. 154(b) by 0 days.

(21) Appl. No.: 10/195,772

(22) Filed: Jul. 12, 2002

(65) Prior Publication Data

US 2003/0062676 A1 Apr. 3, 2003

Related U.S. Application Data

(63) Continuation-in-part of application No. 09/466,004, filed on Dec. 17, 1999, now Pat. No. 6,293,280.
(60) Provisional application No. 60/304,980, filed on Jul. 12, 2001.

(51) Int. Cl.[7] .................................................. A63F 3/00
(52) U.S. Cl. ........................ 273/243; 273/244; 273/259; 273/277
(58) Field of Search ................................ 273/236, 243, 273/252, 277, 287, 244, 259, 453; D21/334; 434/128, 125

(56) References Cited

U.S. PATENT DOCUMENTS

| 566,730 | A | 8/1896 | McCullen |
|---|---|---|---|
| 1,166,977 | A | 1/1916 | Favary |
| 1,199,529 | A | 9/1916 | Collman |
| 1,368,684 | A | 1/1921 | Guise |
| 1,480,780 | A | 1/1924 | Pauley |
| 1,597,806 | A | 8/1926 | Kvare |
| 2,123,343 | A | 7/1938 | Rightsell |
| 2,149,067 | A | 2/1939 | Otero |
| 2,203,562 | A | 6/1940 | Edwards |
| 2,265,529 | A | 12/1941 | Kemp |
| 2,804,123 | A | 8/1957 | Kling |
| 3,180,639 | A | 4/1965 | Cotler et al. |
| D210,183 | S | 2/1968 | Ross |
| 3,428,978 | A | 2/1969 | Johnson |
| 3,477,074 | A | 11/1969 | Bezanis |
| 3,695,565 | A | 10/1972 | Hodges |
| D225,910 | S | 1/1973 | Kurianski |
| 3,729,847 | A | 5/1973 | Chandos |
| 3,740,768 | A | 6/1973 | McCosker |

(List continued on next page.)

FOREIGN PATENT DOCUMENTS

| DE | 3920996 | 5/1990 |
|---|---|---|
| GB | 948667 | 2/1964 |
| GB | 1061321 | 3/1967 |
| GB | 2039406 | 8/1980 |

OTHER PUBLICATIONS

Internet game "Romantic Rendezous" 2 pages (http://www.areyougame.com).*

Primary Examiner—Vishu K Mendiratta
(74) Attorney, Agent, or Firm—Dunlap, Codding & Rogers P.C.

(57) ABSTRACT

The present invention is directed to a kissing shield game and method teaching safe affection to at least one person playing the kissing shield game. The kissing shield game includes a plurality of removable pegs, a playing surface, a gaming member, a plurality of frames and a plurality of thin, flexible membranes forming a kissing shield, and a resetable timer. The playing surface has a plurality of holes arranged in a predetermined pattern with each of the plurality of holes being capable of receiving at least one of the plurality of removable pegs. Each side of the gaming member has a different color associated therewith as well as a predetermined set of alphanumeric symbols associated therewith. The kissing shield is used when a selected person or object determined by a player is kissed so that the player learns safe affection and the proper use of the kissing shield through repetition.

10 Claims, 6 Drawing Sheets

U.S. PATENT DOCUMENTS

| | | |
|---|---|---|
| 3,771,247 A | 11/1973 | DeHarak |
| 3,772,707 A | 11/1973 | Alsoi et al. |
| 3,781,994 A | 1/1974 | Hesselgren |
| 3,802,429 A | 4/1974 | Bird |
| 4,034,495 A | 7/1977 | Lemelson |
| 4,050,457 A | 9/1977 | Davidson |
| 4,084,585 A | 4/1978 | Venaleck |
| D265,327 S | 7/1982 | Okamoto |
| 4,486,975 A | 12/1984 | Harreld et al. |
| 4,498,652 A | 2/1985 | Malik |
| 4,583,946 A | 4/1986 | Shanel |
| 4,664,628 A | 5/1987 | Totaro |
| 4,781,709 A | 11/1988 | Grubman |
| 4,815,456 A | 3/1989 | Rubin et al. |
| 4,825,878 A | 5/1989 | Kuntz et al. |
| 4,837,861 A | 6/1989 | Cole |
| 4,856,535 A | 8/1989 | Forbes |
| 4,872,465 A | 10/1989 | Kuntz et al. |
| 4,944,312 A | 7/1990 | Smith |
| 4,974,605 A | 12/1990 | Esqueda |
| 5,067,723 A * | 11/1991 | Yurkovic .................... 273/249 |
| 5,078,409 A * | 1/1992 | Butler et al. ................ 273/459 |
| 5,112,322 A | 5/1992 | Hathaway |
| 5,423,550 A * | 6/1995 | Guthrie ..................... 273/247 |
| 5,727,565 A * | 3/1998 | Wood ......................... 128/857 |

* cited by examiner

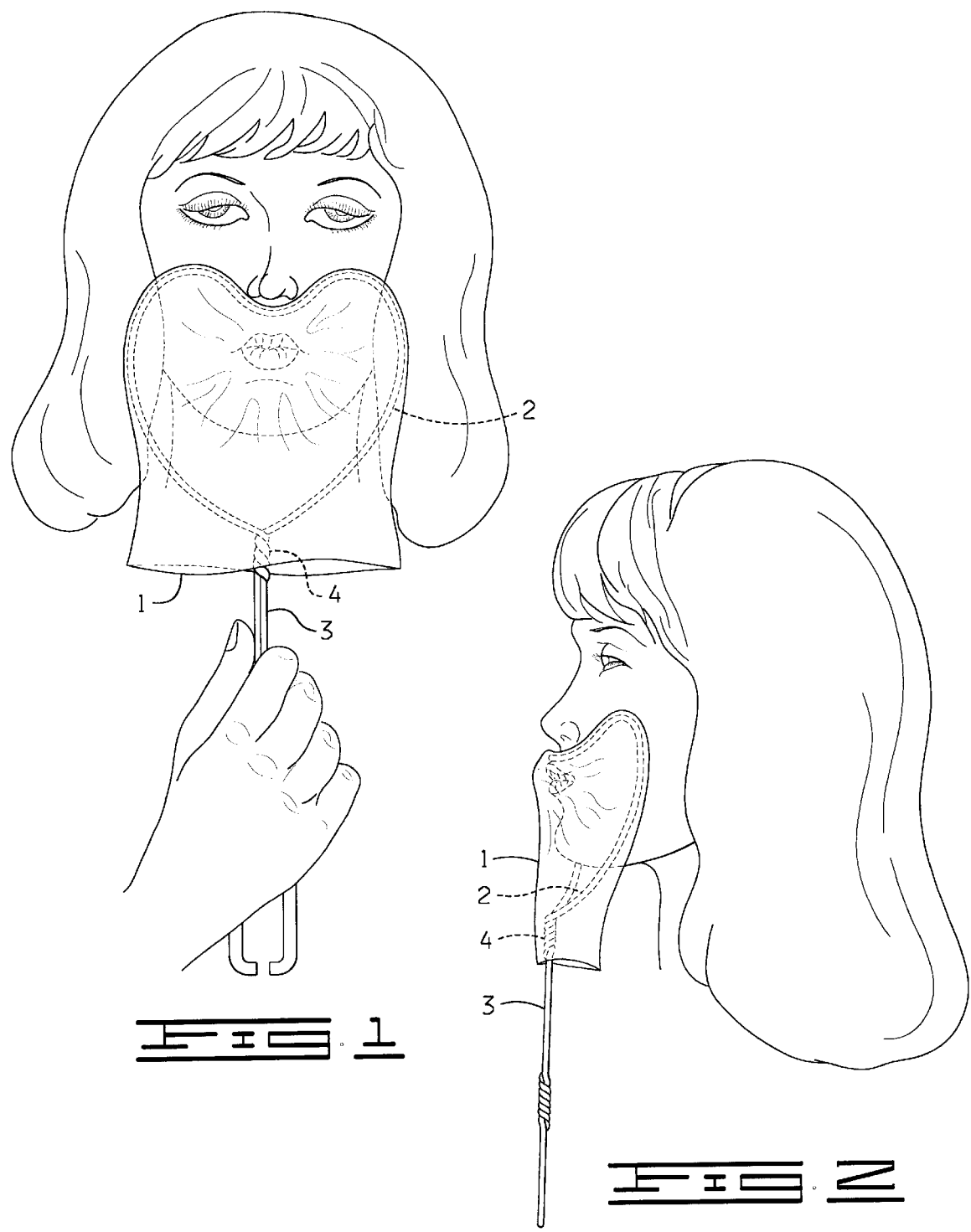

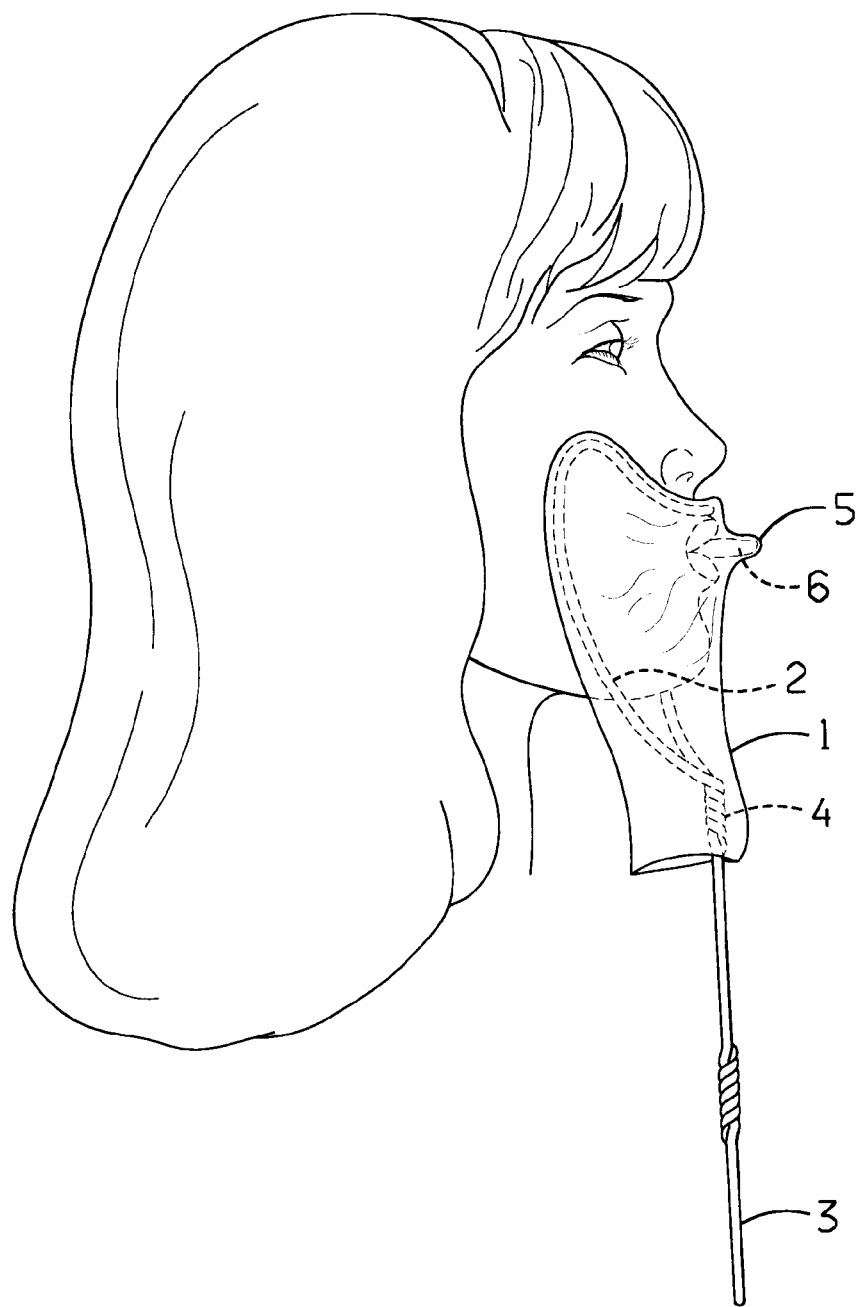

KISSING SHIELD GAME AND METHOD OF USE THEREOF

CROSS REFERENCE TO RELATED APPLICATIONS

This application claims benefit under 37 CFR 119(e) of U.S. Provisional No. 60/304,980, filed Jul. 12, 2001, entitled "KISSING SHIELD GAME;" and is also a continuation-in-part of U.S. Serial No. 09/466,004, filed Dec. 17, 1999, entitled "KISSING SHIELD AND METHOD OF USE THEREOF," now U.S. Pat. No. 6,293,280, the contents of both are hereby incorporated herein in their entirety by reference.

STATEMENT REGARDING FEDERALLY SPONSORED RESEARCH OR DEVELOPMENT

Not Applicable.

BACKGROUND OF THE INVENTION

1. Field of the Invention

The present invention relates generally to a board game, and more particularly, but not by way of limitation, to a board game for teaching a person to practice safe affection utilizing a kissing shield and playing pieces.

2. Description of Background of Invention

There is a growing awareness of the seriousness of diseases, like Acquired Immunodeficiency Syndrome (AIDS), being spread and the need for protection of those not exposed to such diseases. At times, there has been hysteria among parents and other students, who are afraid their children or they themselves will become infected from classroom and playground contact, when students with AIDS or the Human Immunodeficiency Virus (HIV) have attended school. Also, persons who carry the herpes virus sometimes have lip sores which are usually not distinguishable from an ordinary canker sore or a fever blister by a lay person.

It is customary when we kiss to come in contact with another's lips, and in certain cultures, to follow with a kiss on the skin of each cheek; thus germs can be passed from one person to another. In keeping with one aspect of the invention, if casual contact is necessary and a kiss is appropriate, one can protect oneself from the germs present in saliva or other secretions which might be transmitted from kissing by using a kissing shield.

The present invention proposes using a device in which a flexible membrane is used as a kissing shield to lessen one's chances of becoming infected by disease from casual contact. In the alternative, if a person is infected, the chances of transferring the infectious disease from one person to another could be reduced by use of a thin, resilient flexible, impervious membrane, preferably selected from the class of polyethylene, vinyl, and polypropylene materials, stretched over a frame or holder. This would lessen the spread of bodily fluids from one person to another when kissing with the end result of preventing the spread of viruses and diseases, such as canker sores, fever blisters, and AIDS, until there is a cure and prevention of the diseases. The advantages of a kissing shield over regular kissing will become apparent on consideration of the following specification and the accompanying drawings wherein there is disclosed a preferred embodiment.

The kissing shield has both social and health benefits, if basic precautions, such as those one would engage in while using a condom to practice "safe sex", or as a dentist would use when he dons rubber gloves to prevent bodily fluids, such as blood and saliva from his patient, from spreading to his hands and thereby infecting him, are used. The kissing shield can be economically mass produced so that it could be easily disposed of after kissing a person and replaced with a new one.

The kissing shield is for people who desire to be cautious when in contact with another person as they kiss. Use of the kissing shield is convenient and practical. However, like most items we use when we must alter our habits, education is an important step. The kiss is one of the first forms of affection that we display to another. It seems only natural that we would start at a fundamental level and teach "safe kissing" before we teach "safe sex".

The kissing shield, if handled properly, will help people who want to do whatever they can while kissing to practice "preventive medicine" and ensure that disease is not passed from one person to another by proper sanitation or cleanliness of one or both parties. A person who might have a disease and a person who does not want to get the disease or a person who is being protected would take precautionary moves to help prevent the spread of diseases, such as AIDS, by first practicing "safe kissing". A kissing shield is for casual kissing. It can be used especially by a politician who kisses babies.

It is therefore a primary object of the invention to provide a simple, inexpensive kissing shield to be used when kissing mouth-to-mouth or mouth-to-cheek thereby avoiding the necessity for skin contact with the person to whom affection is intended. It is another object of the invention to provide a means for removing the hesitancy a user may have in kissing another individual without sacrificing the effectiveness of the kiss. It is a further object of the invention to provide a means of preventing the transmission of germs or viruses from saliva or other secretions and the transfer of lipstick or other cosmetics when individuals are engaged in kissing. It is another object of the invention to provide a shield which does not need to be worn. It is another object of the invention to provide a shield which is economical in construction, such that the device can be used once and thereafter disposed of.

In addition, board games have traditionally been used as a form of recreational activity. The typical board game has a playing surface which provides the means on which the board game is played. Additionally, the board game is provided with accessories in the form of instruction cards, figures, dice, etc. The playing of the board game is dictated by a set of rules or instructions which refer to the movement of selected accessory parts around the playing surface. Board games are traditionally played by more than one person either as a group of individuals or in teams of defined size and are enjoyed by some families and groups as a form of recreational activity.

However, board games do not solely function as an alternative recreational activity. Many board games provide a teaching means to improve a person's general knowledge and education. To this end, a need exists for a board game utilizing the kissing shield that teaches safe affection. It is to such a board game that the present invention is directed.

SUMMARY OF THE INVENTION

The present invention is directed to a kissing shield game and method for teaching safe affection to at least one person playing the kissing shield game. The kissing shield game includes a plurality of removable pegs, a playing surface, a gaming member, a plurality of frames, a plurality of thin, flexible membranes, and a resetable timer.

The playing surface has a plurality of holes. Each of the plurality of holes is capable of receiving at least one of the plurality of removable pegs which may be colored. The plurality of holes are arranged in a predetermined pattern. The gaming member has at least two sides. Each of the sides of the gaming member has a different color associated therewith as well as a predetermined set of alphanumeric symbols associated therewith. Each color associated with one of the sides of the gaming member is assigned a predetermined numerical value. In addition, at least one of the removable pegs is colored to correspond to at least one of the colors on at least one of the sides of the gaming member.

The plurality of frames are so dimensioned as to outline the mouth of a person. Each of the plurality of frames has a loop formed into a heart shape such that each lobe of the heart shape outlines a cheek area of the person. The nose of the person is positioned between the lobes of the heart shape, and the point of the heart shape extends to or below the chin of the person. The plurality of frames further have a handle extending therefrom and adapted for being gripped by a user to support the frame.

The plurality of thin, flexible membranes are carried by each of the plurality of frames and are impervious to microorganisms. Each of the plurality of thin, flexible membranes prevents exchange of microorganisms between the person and an object while engaged in the act of kissing.

In addition, the kissing shield game includes a set of rules which govern the function of the kissing shield game and the order and actions of a kissing shield game participant. A plurality of persons may be divided into a plurality of teams for playing the kissing shield game.

In use, at least one of the thin, flexible membranes is placed over at least one of the plurality of frames so as to form a kissing shield. The gaming member is thrown along the playing surface so that one of the sides lands facing in an upward direction. A role playing adventure is determined within a predetermined time so as to teach safe affection in accordance with the alphanumeric symbol associated with the side of the gaming member facing in an upward direction. A selected person or object determined by the player is kissed with the kissing shield so that at least one person playing the kissing shield game learns safe affection and the proper use of the kissing shield through repetition. The end of the predetermined time is signaled by the resetable timer. A number is determined for sequential movement of at least one of the plurality of removable pegs in accordance with a predetermined number associated with the color of the side of the gaming member facing in the upward direction. If a role playing adventure is determined, then at least one of the removable pegs is moved in a forward direction along the plurality of holes arranged in the predetermined pattern in accordance with the predetermined number associated with the color of the side of the gaming member facing in an upward direction. However, upon the person playing the kissing shield game failing to determine the role playing adventure within a specified time, then at least one of the removable pegs is moved in a backward direction along the plurality of holes arranged in the predetermined pattern in accordance with the predetermined number associated with the color of the side of the gaming member facing in an upward direction. At least one of the removable pegs lands in at least one of the plurality of holes in accordance with the predetermined number associated with the color of the side of the gaming member facing in an upward direction. A kissing shield game winning player is determined based upon the first person playing the kissing shield game to advance in a forward direction along the plurality of holes in the predetermined pattern on the playing surface until the plurality of holes in the predetermined patten ends.

The advantages and features of the present invention will become apparent to those skilled in the art when the following description is read in conjunction with the attached drawings and the appended claims.

BRIEF DESCRIPTION OF THE SEVERAL VIEWS OF THE DRAWINGS

FIG. 1 shows a front plan view of a kissing shield placed over the frame or holder and held in position by a user for use.

FIG. 2 is a side plan view of the kissing shield shown in FIG. 1.

FIG. 3 is a side plan view of an embodiment of the kissing shield wherein the kissing shield has a protuberance for the tongue.

DETAILED DESCRIPTION OF THE INVENTION

Figure 4:
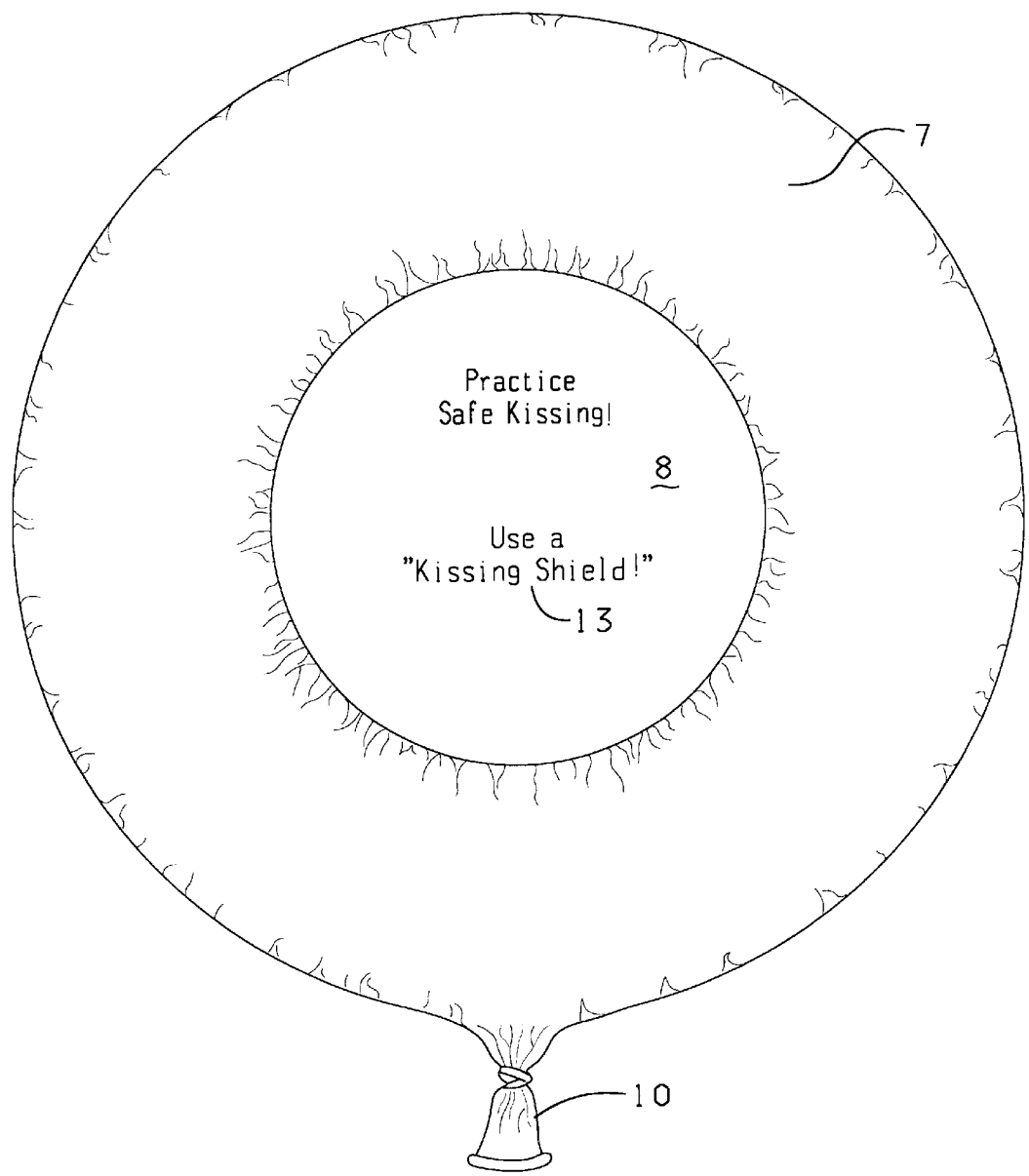
FIG. 4 shows a balloon shaped kissing shield having a center web with indicia to inform the user.

Referring now to the drawings wherein like reference characters represent like elements, FIG. 1 shows a thin, flexible, impervious membrane 1 placed over a frame 2 and positioned in the appropriate location for use. Membrane 1 is closed on three sides; a fourth side remains open so that the shield may be placed over frame 2. Membrane 1 may be selected from the group of thin, flexible, impervious materials, such as polyethylene, vinyl, and polypropylene. Holder 2 is comprised of a handle 3 and a crook 4. Crook 4 is cordate so that it can be placed under the nose of the user while protecting the cheeks, lips, and chin of the user. Handle 3 extends laterally from crook 4 and is sized so that when the user grasps the device, his hand will be located at a distance rom the membrane. It will be appreciated that membrane 1/frame 2 can be sized to be employed by a variety of users. As shown in FIG. 2, crook 4 is adapted to surround the lower part of the face of the user.

FIG. 3 shows thin, flexible, impervious membrane 1 having a protuberance 5 located near the uppermost portion of membrane 1. Protuberance 5 creates a space 6 into which the tongue of a user may be placed for a particular type of kissing.

FIG. 4 shows a balloon shaped embodiment of the present invention. In this particular embodiment, a membrane 8 is located within a donut-shaped, circular frame 7. As illustrated, a message could be located within membrane 8 for the purpose of informing the user of the proper side of the device to place against his face, among other things. It would be desirable to have the message printed on the inside of a clear membrane so as to prevent the lips from kissing the printed message.

Figure 5:
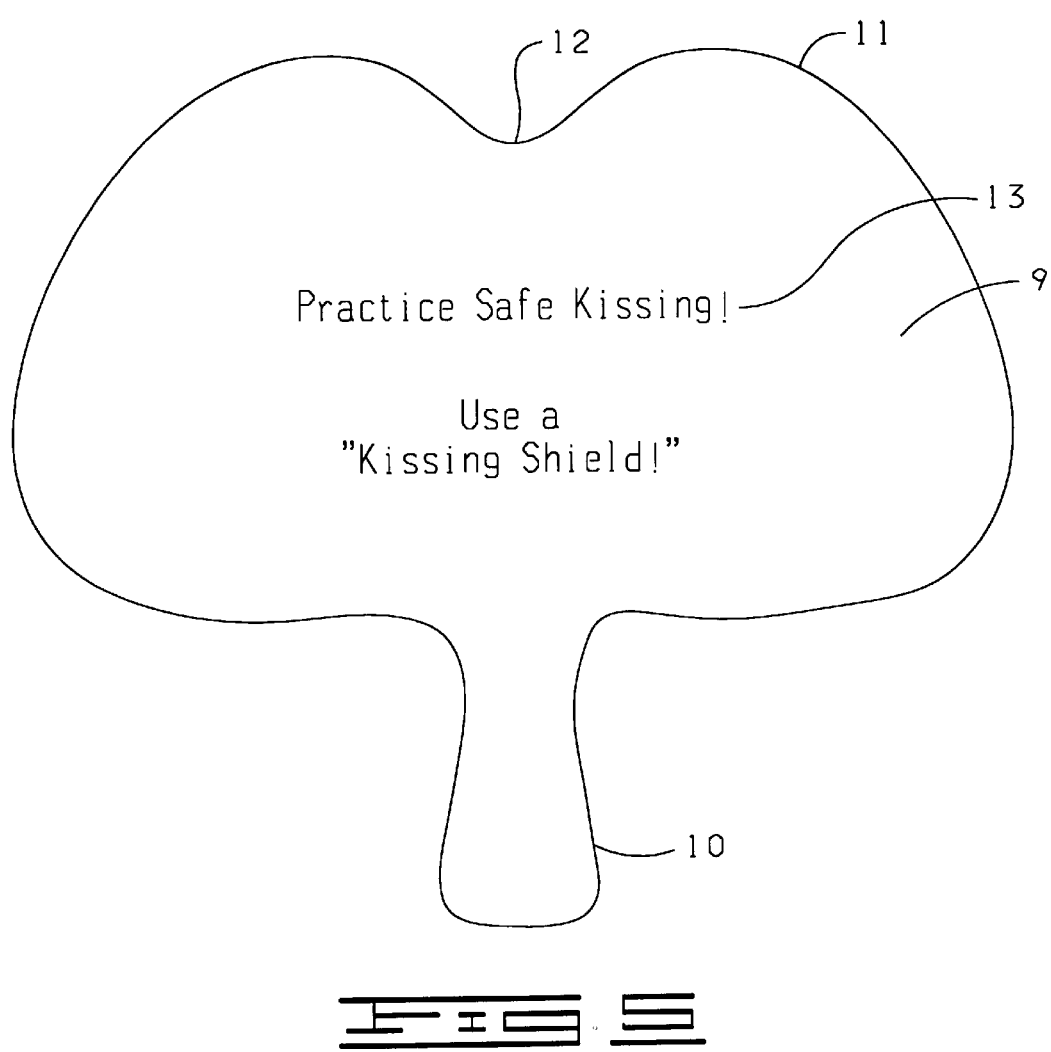
FIG. 5 shows a toy kissing shield.

FIG. 5 shows a flexible, plastic sheet 9 suitable for use by a child. Sheet 9 is shaped to include a handle 10, a flexure 11 to cover the cheeks of the child, and a depression 12 suitable for placement under the nose of the user. A message 13 is centered on sheet 9. Handle 10 extends laterally from flexure 11 and is sized so that when the device is used, the hand of the user will be spaced apart from flexure 11.

A kissing shield game includes a plurality of removable pegs 15, a playing surface 16, a gaming member 18, a plurality of frames 2 (FIGS. 1–3), a plurality of thin, flexible membranes 1 (FIGS. 1–3), and a resetable timer 100.

Figure 6:
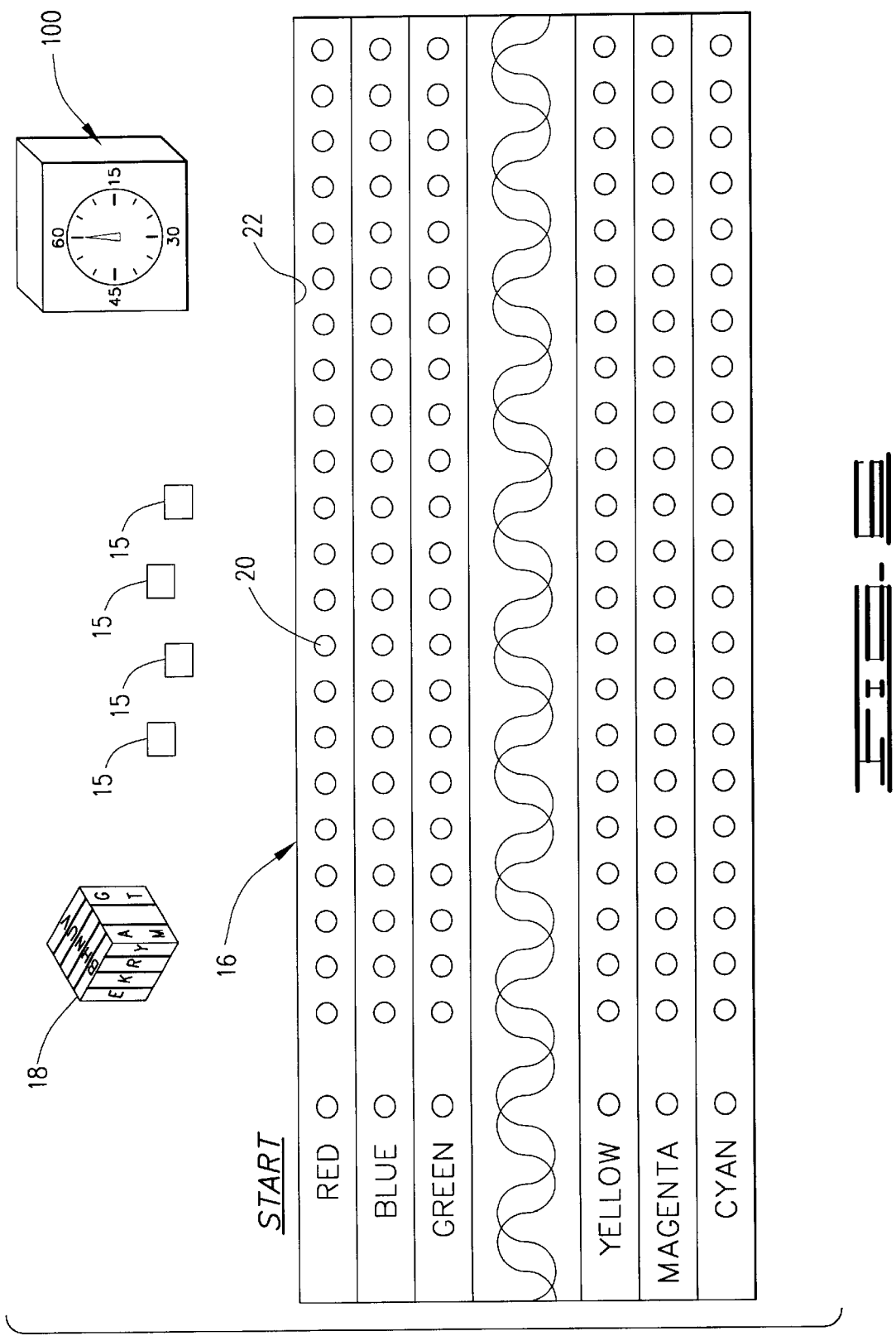
FIG. 6 shows a top view of a playing surface of a kissing shield game.

Referring now to FIG. 6, the playing surface 16 has a plurality of holes 20. Each of the plurality of holes 20 is capable of receiving at least one of a plurality of removable pegs 15 which may be colored. In addition, each of the plurality of frames 2 may also be colored. Any color may be used for the plurality of removable pegs 15, however, the color of each of the plurality of removable pegs 15 will preferably correspond to the color of the frame 2. Examples of colors that may be used for the removable pegs 15 and the plurality of frames 2 in the kissing shield game consist of red, blue, green, yellow, magenta, and cyan.

The plurality of holes 20 are arranged in a predetermined pattern. The predetermined pattern is preferably in a row 22, as shown in FIG. 6. However, it should be understood that the pattern may be any of a variety of patterns, such as diagonals, waves, or circles and as such should not be regarded as limiting.

Figure 7:
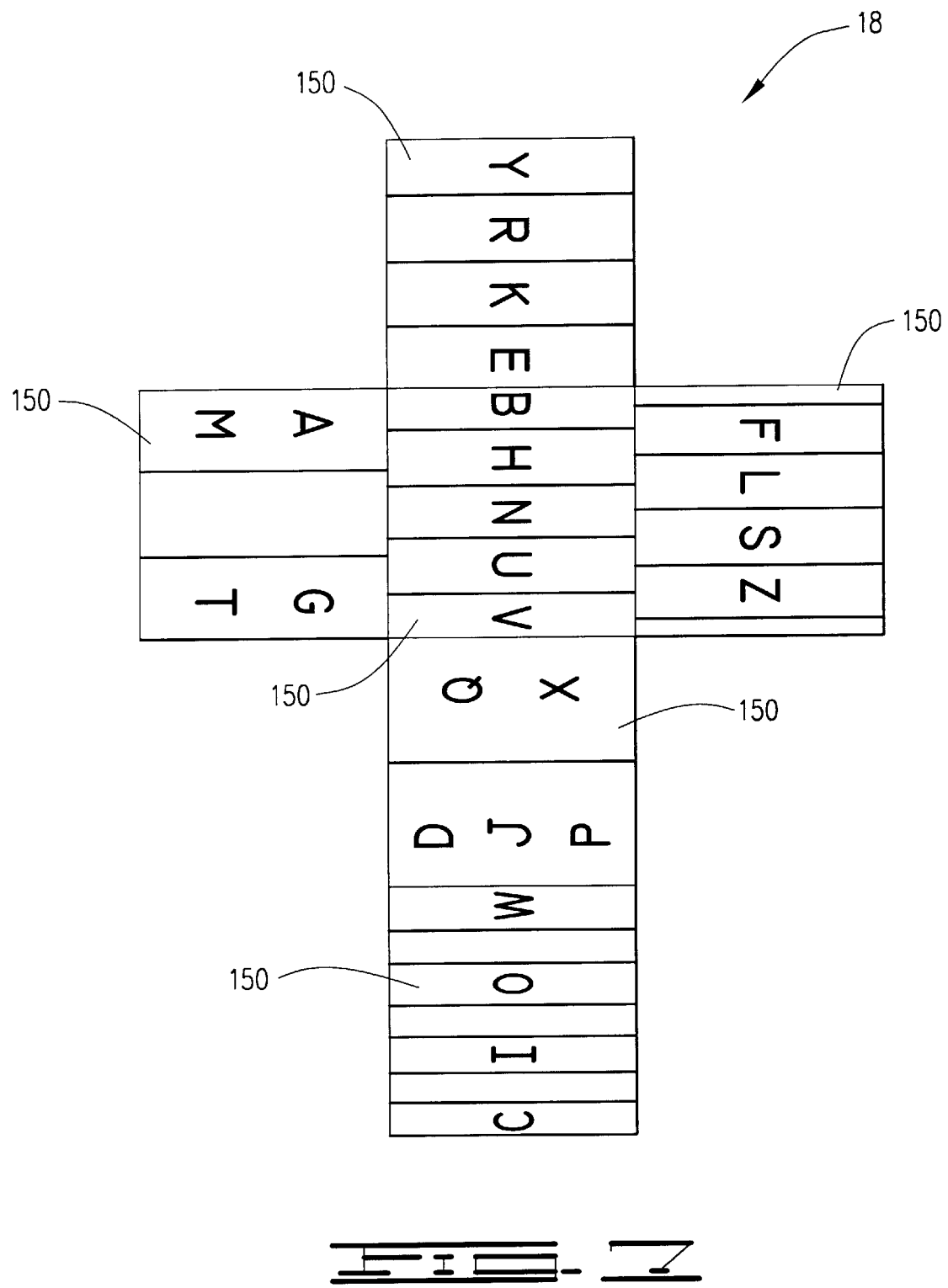
FIG. 7 shows a flat view of mulitple sides of a gaming member used in the kissing shield game.

Shown in more detail in FIG. 7, the gaming member 18 has at least two sides. FIG. 7 shows the gaming member 18 having six sides, however, it should be understood that the gaming member may have any number of sides as long as there are at least two. Each of the sides of the gaming member 18 has a different color associated therewith as well as a predetermined set of alphanumeric symbols 150 associated therewith. Any color may be used in the kissing shield game. Examples of preferred colors include green, cyan, blue magenta, red, and yellow. Each color associated with one of the six sides of the gaming member 18 is assigned a predetermined numerical value. For example, green-6, cyan-5, blue-4, magenta-3, red-2, and yellow-1. The predetermined numbers determine how many of the plurality of holes 20 the removable pegs 15 will be moved. In addition, each side of the gaming member 18 may have four or six different letters of the alphabet.

In use, the gaming member 18 is thrown by a player along the playing surface 20 so that one of the sides lands facing in an upward direction. The player determines a role playing adventure according to the side of the gaming member 18 that faces upward. The role playing adventure corresponds to one of the alphanumeric symbols 150 that are shown on the side of the gaming member 18 that is facing upward. For example, if the side of the gaming member 18 that is facing upward has a "c" showing, then the user must select a role playing adventure that begins with the letter "c", e.g. kissing a cat. The player has a predetermined time to decide what sort of role-playing will be done so as to teach safe affection. A selected person or object determined by the player is kissed with the kissing shield so that at least one person playing the kissing shield game learns safe affection and the proper use of the kissing shield through repetition. So, for example, the player rolls the gaming member 18 and the gaming member 18 lands with one of the six sides facing upward that is green with the letters C, I, O and W. The player then determines a person or object beginning with one of the letters to kiss with the kissing shield.

The end of the predetermined time is signaled by the resetable timer 100 and a number is determined for sequential movement of at least one of the plurality of removable pegs 15 in accordance with a predetermined number associated with the color of the side of the gaming member 18 facing in the upward direction. If the player is successful in and acting out the role playing adventure, then the player may move the removable peg 15 in a forward direction along the plurality of holes 20 arranged in the predetermined pattern in accordance with the predetermined number associated with the color of the side of the gaming member 18 facing in an upward direction. Thus, if the numerical value six was assigned to the color green, green being the side of the gaming member 18 landing face up, then the player moves the removable peg 15 six holes forward along the plurality of holes 20. However, if the player does not determine and act out the role playing adventure within the specified time, then at least one of the removable pegs 15 (associated with the player) is moved in a backward direction along the plurality of holes 20 in accordance with the predetermined number associated with the color of the side of the gaming member 18 facing in an upward direction. So, the removable peg 15 will be moved six holes backward according to the example given above if no role playing adventure is determined and acted out. At least one of the removable pegs 15 lands in at least one of the plurality of holes 20 in accordance with the predetermined number associated with the color of the side of the gaming member 18 facing in an upward direction. A kissing shield game winning player is determined based upon the first person playing the kissing shield game to advance his/her removable peg 15 in a forward direction along the plurality of holes 20 in the predetermined pattern on the playing surface 16 until the plurality of holes 20 in the predetermined patten ends.

In view of the above, it will be seen that the several objects of the invention are achieved and that other advantageous results are attained. As various changes could be made in the above product and method without departing from the scope of the invention, it is intended that all matter contained in the above description or shown in the accompanying drawings shall be interpreted as illustrative and not in a limiting sense.

It should be noted that the foregoing drawings and accompanying descriptions are intended to be exemplary of several preferred embodiments of the invention and are not exhaustive of the possibilities of the types of shields within the intended scope of the invention. It should also be understood that modifications will readily occur to those skilled in the art within the spirit of the invention. Such modifications could include using different color materials on each side of the membrane or sheet to ensure that the user consistently originates his kisses from the same side of the membrane. The frame or holder onto which the thin, flexible, impervious membrane is placed could be made of a plastic material, such as nylon, so that it could be sanitized for use by different people. The frame or holder might also be made of a firm, yet flexible material which would allow the device to be adjusted or shaped by the user for individual faces. The membrane could also be made of a plastic material which would be unaffected by products, such as foundation, lipstick, petroleum jelly, and other cosmetics routinely used by most women.

What is claimed is:

1. A kissing shield game, comprising:
    a plurality of removable pegs;
    a playing surface having a plurality of holes, wherein each of the plurality of holes is capable of receiving at least one of the plurality of removable pegs, the plurality of holes further being arranged in a predetermined pattern;
    a gaming member having at least two sides, wherein each of the sides of the gaming member has a different color associated therewith as well as a predetermined set of alphanumeric symbols associated therewith;

a plurality of frames so dimensioned as to outline the mouth of a person, each of the plurality of frames having a loop formed into a heart shape such that each lobe of the heart shape outlines a cheek area of the person, the nose of the person positionable between the lobes of the heart shape, and the point of the heart shape extending to or below the chin of the person, the plurality of frames further having a handle extending therefrom and adapted for being gripped by a user to support the frame;

a plurality of thin, flexible membranes carried by each of the plurality of frames and impervious to microorganisms, each of the plurality of thin, flexible membranes preventing exchange of microorganisms between the person and an object while engaged in the act of kissing; and a resetable timer.

2. The kissing shield game of claim 1, wherein each color associated with one of the sides of the gaming member is assigned a predetermined numerical value.

3. The kissing shield game of claim 1, further comprising a set of rules which govern the function of the kissing shield game and the order and actions of a kissing shield game participant.

4. The kissing shield game of claim 1, wherein a plurality of persons may be divided into a plurality of teams for playing the kissing shield game.

5. The kissing shield game of claim 1, wherein each of the plurality of frames is colored and at least one of the removable pegs is colored to correspond to the color of at least one of the plurality of frames.

6. A method for teaching safe affection to at least one person playing a kissing shield game, the method comprising the steps of:

providing a kissing shield game, comprising:
a plurality of removable pegs;
a playing surface having a plurality of holes, wherein each of the plurality of holes is capable of receiving at least one of the plurality of removable pegs, the plurality of holes further being arranged in a predetermined pattern;
a gaming member having at least two sides, wherein each of the sides of the gaming member has a different color associated therewith as well as a predetermined set of alphanumeric symbols associated therewith;
a plurality of frames so dimensioned to outline the mouth of a person, each of the plurality of frames having a loop formed into a heart shape such that each lobe of the heart shape outlines a cheek area of the person, the nose of the person positionable between the lobes of the heart shape, and the point of the heart shape extending to or below the chin of the person, the plurality of frames further having a handle extending therefrom and adapted for being gripped by a user to support the frame;
a plurality of thin, flexible membranes carried by each of the plurality of frames and impervious to microorganisms, each of the plurality of thin, flexible membranes preventing exchange of microorganisms between the person and an object while engaged in the act of kissing; and
a resetable timer;

placing at least one of the thin, flexible membranes over at least one of the plurality of frames so as to form a kissing shield;

throwing the gaming member along the playing surface so that one of the sides lands facing in an upward direction;

determining a role playing adventure within a predetermined time so as to teach safe affection utilizing the kissing shield as a means to block contact between the person and an object in accordance with the alphanumeric symbol associated with the side of the gaming member facing in an upward direction, the end of the predetermined time being signaled by the resetable timer;

determining a number for sequential movement of at least one of the plurality of removable pegs in accordance with a predetermined number associated with the color of the side of the gaming member facing in the upward direction; and landing in at least one of the plurality of holes in accordance with the predetermined number associated with the color of the side of the gaming member facing in an upward direction.

7. The method of claim 6, further including the step of kissing a selected person or object determined by the player with the kissing shield so that at least one person playing the kissing shield game learns safe affection and the proper use of the kissing shield through repetition.

8. The method of claim 6, further including the step of moving at least one of the removable pegs in a forward direction along the plurality of holes arranged in the predetermined pattern in accordance with the predetermined number associated with the color of the side of the gaming member facing in an upward direction.

9. The method of claim 6, further including the step of moving at least one of the removable pegs in a backward direction along the plurality of holes arranged in the predetermined pattern in accordance with the predetermined number associated with the color of the side of the gaming member facing in an upward direction upon the person playing the kissing shield game failing to determine the role playing adventure within a specified time.

10. The method of claim 6, further including the step of determining a kissing shield game winning player based upon the first person playing the kissing shield game to advance in a forward direction along the plurality of holes in the predetermined pattern on the playing surface until the plurality of holes in the predetermined patten ends.

* * * * *

UNITED STATES PATENT AND TRADEMARK OFFICE
CERTIFICATE OF CORRECTION

PATENT NO. : 6,789,799 B2 Page 1 of 1
DATED : November 3, 2005
INVENTOR(S) : Deloris Gray Wood It is certified that error appears in the above-identified patent and that said Letters Patent is hereby corrected as shown below:

Column 4,
Line 26, after "of" and before "sides" change "mulitple" to -- multiple --.
Line 44, after "distance" and before "the" change "rom" to -- from --.

Signed and Sealed this

Third Day of January, 2006

JON W. DUDAS
*Director of the United States Patent and Trademark Office*